United States Patent [19]

Gavrilin et al.

[11] 4,215,562
[45] Aug. 5, 1980

[54] METHOD FOR DETECTING SURFACE AND SUBSURFACE FLAWS IN ROLLED PRODUCTS

[76] Inventors: Evgeny F. Gavrilin, ulitsa shosse Metallurgov, 53a, kv. 217; Alexandr N. Belokur, ulitsa Degtyareva 40a, kv. 6; Artur L. Daiker, ulitsa, B. Khmelnitskogo, 27, kv. 11; Anatoly E. Konash, ulitsa Molodogvardeitsev, 46, kv. 10; Vladislav V. Basov, ulitsa Stalevarov, 27, kv. 11; Nikolai F. Moskvin, ulitsa Peti Kalmykova, 16, kv. 32, all of Chelyabinsk, U.S.S.R.

[21] Appl. No.: 898,424

[22] Filed: Apr. 19, 1978

[51] Int. Cl.$^2$ ............................................. G01N 25/72
[52] U.S. Cl. .................................................. 73/15 FD
[58] Field of Search ............................. 73/15 FD, 356; 116/114 V, 209

[56] References Cited

U.S. PATENT DOCUMENTS 3,020,745 2/1962 Sielicki ............................... 73/15 FD
3,511,086 5/1970 Woodmansee .................... 73/15 FD
4,109,508 8/1978 Fukuyama ........................ 73/15 FD

OTHER PUBLICATIONS

Kutzscher et al., "Thermal and Infrared Methods for Nondestructive Testing of Adhesive-Bonded Structures"–Materials Evaluation–Jul. 1968, pp. 143-148.

Primary Examiner—Charles A. Ruehl
Attorney, Agent, or Firm—Haseltine, Lake & Waters

[57] ABSTRACT

A method for detecting surface and subsurface flaws in rolled products in which an indicator coating is applied to the surface of a rolled product, whereupon the coated surface is heated with high-frequency currents. The high-frequency heating produces a temperature gradient between good and defective portions of the blank, which is sufficient to bring about a thermochemical transformation of the indicator coating over the defective areas, accompanied by a change in the color of the coating in those areas. Dark spots on the light coating indicate the locations of surface and subsurface flaws. The sharp images of flaws are visible over a long period of time on the surface of the rolled product, which makes it possible to dispense with the marking of flaws. The defective areas thus identified are chipped.

8 Claims, 1 Drawing Figure

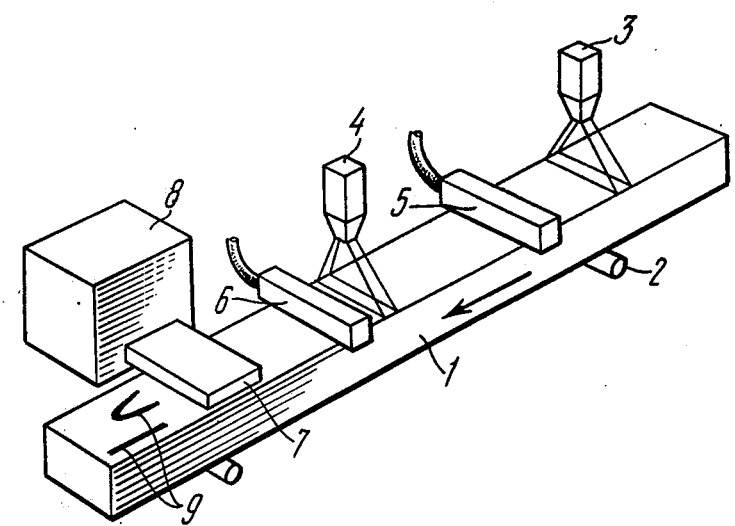

METHOD FOR DETECTING SURFACE AND SUBSURFACE FLAWS IN ROLLED PRODUCTS

FIELD OF THE INVENTION

The present invention relates to methods for nondestructive quality inspection of the surface of metal articles and, more particularly, to a method for detecting surface and subsurface flaws in rolled products.

This invention is readily adaptable for use in the quality inspection of the surface of hot-rolled blanks and billets (blooms and slabs) without descaling that surface, as well as in the quality inspection of the surface of rolled products of complex sectional configurations, such as rails and beams.

PRIOR ART

Visual inspection is the commonest method for quality inspection of the surface of rolled products used in metallurgy today. The inspector's visual acuity, as well as his skill and experience, are crucial in visual inspection; hence, this method is subjective and cannot give a comprehensive picture of a product's flaws, which is especially true of rolled products with scale-coated surfaces. As a result, the chipping of defective areas covers a surface a number of times larger than that of the defective areas.

The requirements imposed upon the quality of metal articles by the leading industries are becoming increasingly stringent and call for reliable methods for quality inspection of both finished rolled articles and products that are to undergo further rolling operations. A detection and elimination of surface defects in blanks, effected as early as possible in the course of a rolling or rerolling process, is a good guarantee of the absence of defects in finished products.

An early detection of surface flaws in articles intended for rerolling makes it possible to clean only defective areas instead of cleaning the entire surface of a blank, which reduces the amount of labor put into the cleaning operations, as well as losses of metal.

At present, the quality inspection of the surface of rolled products has been automated and is based on a number of tests used throughout the world. The basic tests are magnetic powder, magnetographic and eddy current tests.

The magnetographic and eddy current tests have limited application because they impose stringent requirements on the surface conditions of blanks, such as the curvature, scalops, etc. As a rule, these methods require descaling; another limitation for their use is the presence of sharp edges in a rolled product, or surface defects with sharp edges.

Thus the magnetographic and eddy current tests are only applicable to etched and pretreated surfaces.

The magnetic powder test does not necessitate descaling, but has a relatively low sensitivity; the minimum depth of defects detected with the aid of this latter method is as great as 0.5 to 1.0 mm.

When used for checking billets of rectangular sections, the magnetic powder method displays different sensitivities at the edges and side faces of billets.

One of the basic disadvantages of the magnetic powder test is that it necessitates the presence of an inspector who visually detects and marks flaws; as a result, the method is not quite objective. Another disadvantage is the necessity of using UV radiation for flaw detection.

A common disadvantage of all the three electromagnetic tests is that neither of them makes it possible to detect subsurface defects.

Another method for detecting surface flaws in metal articles is referred to as the capillary technique. An article to be checked is wetted with a coloring liquid (a penetrant), washed and dried. The article is then coated with a layer of a white quick-drying substance (a background component). Where the penetrant gets into cavities or other surface defects it shows against the white background as a red spot or a spot of some other color. As a result, all the defects are effectively identified.

There is known a method for checking welded joints (cf. Konstr.Elem. Meth., 1973, März), whereby a solution of lime or chalk is applied onto one side of a welded joint, whereupon this side is dried; applied onto the opposite side of the welded joint is a petroleum-based liquid. All the cracks in the joint become visible against the white background.

There is further known a method for detecting surface flaws in metal articles (cf. Federal Germany Pat. No. 1,951,947, Cl. 42K 46/01, 1971), whereby a penetrating indicator dying agent is applied onto the surface of an article being checked, whereupon the agent is removed from the articles's surface to be replaced by a layer of a developing adsorbent dissolved in a quick-drying liquid. The presence of brightly colored spots and streaks is indicative of defects in the article.

There is still further known a method for detecting surface flaws in metal articles (cf. U.K. Pat. No. 1,326,255, Cl. GiS, published Mar. 8, 1973). According to this method, a special penetrating compound is applied onto the surface of an article to be checked, whereupon the excess of that compound is removed and the surface is dried. A layer of a developer is then applied onto the surface of the article. The developer contains a compound which fluoresces when exposed to UV radiation. When the penetrating compound reacts with the developer the latter is no longer fluorescent in UV rays. As a result, there are dark spots against the fluorescent background, which are indicative of flaws in the article.

The foregoing description of different versions of the capillary technique makes it clear that this technique, too, has a number of disadvantages. The most important ones are as follows:

the surface of the article to be checked must be preconditioned (cleaned, washed, etc.);

the testing process is too complicated, which makes it hard and, in certain cases, totally impossible to run quality tests on a continuous basis;

the pinpointing of flaws is hard to effect and depends upon the skill, experience and ability of the inspector;

prior to checking, rolled products must be descaled;

flaw marking means must be used to identify the location of flaws in big rolled products;

finally, the rate of quality inspection is quite low.

SUMMARY OF THE INVENTION

It is an object of the present invention to provide a simple and effective method for detecting surface and subsurface flaws in hot-rolled products without any preconditioning of their surface.

It is another object of the invention to make it possible to automatically mark the location of flaws in rolled products of any size.

It is still another object of the invention to increase the rate of quality inspection of rolled products' surfaces.

It is yet another object of the invention to cut down the cost of quality inspection of the surface of rolled products.

Finally, it is an object of the invention to improve the working conditions of those engaged in quality inspection of surfaces of rolled products.

The foregoing and other objects of the present invention are attained by providing a method for detecting surface and subsurface flaws in rolled products, whereby an indicator coating, comprising a background component and a contrast component, is applied onto the surface of a rolled product, which method is characterized, in accordance with the invention, by that the contrast component is a heat-sensitive compound which changes its color at a certain temperature, and by that the indicator coating is applied when the temperature of the rolled product is relatively low, whereupon the rolled product is heated with high-frequency currents to a temperature sufficient to produce a temperature gradient, whereby in defective areas of the rolled product there takes place a thermochemical transformation of the contrast component of the coating, accompanied by a change in the color of that contrast component.

The proposed method makes it possible:

to check rolled products of any section;

to detect flaws in scale-coated rolled products, as well as in rolled products having their surfaces cleaned with an abrasive disc, flame cutter or plasma arc, or by milling;

to detect surface flaws less than 0.2 mm deep;

to detect subsurface flaws at a depth of up to 2 mm;

to check rolled products moving at a speed of 0.4 to 1 meter per second;

to automatically mark the location of flaws on the surface of a rolled product, which, in turn, makes it possible to dispense with special flaw location marking means;

to indicate the configuration of a flaw, keeping in mind that the contrasting image of a flaw is an exact replica of its configuration.

An important feature of the invention is the use of heating with high-frequency currents. This type of heating results in an increased eddy current density at places where the material of a rolled article loses its continuity, i.e. in defective areas. Thus the defective areas are heated to a higher temperature than the rest of the material, which results in a local overheating in the defective areas. The gradient of temperatures between good and defective portions of the rolled product's surface is great enough to cause a thermochemical transformation of the contrast component of the indicator coating over the defective areas. The color of the indicator coating is changed in these areas, whereas it remains the same over the rest of the product's surface.

The heating time or the speed at which a rolled product moves relative to the inductor are selected so as to produce sharp images of defects; on the other hand, the color of the indicator coating over the rest of the product's surface must be intact or changed to a negligible degree.

It is expedient that the background component of the indicator coating should be a compound of a light color which does not change over a broad rage of temperatures, such as aqueous solution of calcium hydroxide, aqueous solution of chalk, etc.

It is expedient that the contrast component of the indicator coating should be a compound which undergoes a thermochemical transformation with a change in color at a temperature of 200° to 300° C., such as aqueous solution of potato starch.

The indicator coating may be applied onto the surface of a rolled article by successively applying the background and contrast components onto that surface in any manner, for example, with the aid of a brush, dyeing roll or air brush. In such a case the contrast component of the indicator coating may be selected from a broad variety of heat-sensitive compounds.

It is advisable that prior to heating a rolled product with high-frequency currents, the indicator coating should be dried at a temperature not higher than the temperature at which the thermochemical transformation of the contrast component of the indicator coating takes place. As a result, the coating remains relatively intact after the quality checking operations, and the location of defects remains clearly visible over a prolonged period of time it may take before cleaning.

According to a preferred embodiment of the invention, the indicator coating is formed by applying a colloidal suspension to the surface of a rolled product.

This reduces the number of operations involved in the production of the indicator coating and simplifies these operations; on the other hand, only a limited number of heat-sensitive compounds can be used in this case as the contrast component of the indicator coating.

The colloidal suspension may be an aqueous solution of calcium hydroxide and soluble potato starch with the following ratio between the ingredients:

| calcium hydroxide, | 30 to 160 g/l |
|---|---|
| soluble potato starch, | 5 to 20 g/l. |

The above composition of the colloidal suspension accounts for a sufficiently durable indicator coating with sufficiently sharp images of defects which remain visible over a prolonged period of time.

In the proposed colloidal suspension, calcium hydroxide is the background component because its properties and color remain intact over a wide range of temperatures.

Soluble potato starch is the contrast component because it undergoes a thermochemical transformation with a change in color when the surface of the rolled product is heated to a temperature of 250° to 300° C.

The lower limit of the calcium hydroxide concentration must be such as to enable the suspension to cover completely the surface of a rolled product being checked and make the suspension thick enough so as to stay on the product's surface without forming pools. With a calcium hydroxide concentration below the limit of 30 g/l, it is hard to cover the entire surface of the product with suspension; hence, the contrast between good and defective portions of the rolled product is not defined sharply enough for effective fault detection.

Going beyond the upper limit of the calcium hydroxide concentration (160 g/l) is unnecessary because it will produce no positive effect both in terms of the continuity of the coating and the contrast of faults' images against the background.

The lower limit of the starch concentration in the colloidal suspension is selected so as to sharply define faulty areas against the background with the lowermost concentration of calcium hydroxide in the suspension.

Going beyond the upper limit of the starch concentration will not improve the contrast of the faults' images against the background.

The background and contrast components and the colloidal suspension can be applied to the surface of a rolled product in any manner, i.e. by a brush, dyeing roll or air brush.

DESCRIPTION OF THE DRAWING

Other objects and advantages of the present invention will become more apparent from the following detailed description of a preferred embodiment thereof to be read in conjunction with the accompanying drawing the sole FIGURE of which is a schematic view of a device for carrying out the method in accordance with the invention.

DETAILED DESCRIPTION

Referring now to the attached drawing, a blank 1 to be checked is put on a roller bed 2 which is adapted to control the speed of motion of the blank 1 within a range of 0.3 to 1 meter per second. The direction of movement of the blank 1 is indicated by an arrow. Successively arranged in this direction, above the surface of the blank 1, are pulverizers 3 and 4 intended to apply the background and contrast components of the indicator coating, respectively, onto the surface of the blank 1. Placed after the pulverizers 3 and 4, and also above the surface of the blank 1, are nozzles 5 and 6 intended to direct hot air to the surface of the blank 1 so as to dry the background and contrast components, respectively, of the indicator coating.

Arranged after the nozzles 5 and 6, and also above the surface of the blank 1, is an inductor 7 which is electrically coupled to a high-frequency generator 8.

For the sake of simplicity, the drawing shows a device intended for detecting surface and subsurface defects on only one side of the blank 1, although it is apparent that one can simultaneously check all the four faces, as well as the edges, of the blank 1. In such a case, the number of the pulverizers 3 and 4 and nozzles 5 and 6 must correspond to that of the faces of the blank 1 to be checked, while the inductor 7 is to encompass all the sides of the blank 1.

The preferability of checking only one or all sides of a rolled product for surface and subsurface flaws depends upon the type and purpose of the product, as well as upon the manner in which the defects are to be eliminated.

Devices of the type shown in the attached drawing can be employed for detecting surface and subsurface defects in metal articles of any cross-sectional profile, including rails, beams, tubular and sheet products.

When colloidal suspension of the proposed composition is used to produce an indicator coating, the device for checking the surface of rolled products comprises a single pulverizer 4 for applying the suspension onto the surface of products being checked, and a single nozzle 6 for drying the suspension.

Prior to checking, the components of the indicator coating are prepared. The background component may be an aqueous solution of calcium hydroxide with a density of 1.12 to 1.15 g/cm$^3$. The contrast component is an aqueous solution of soluble potato starch with a concentration of 10%. The solutions are prepared by mixing the aforesaid ingredients with water.

The colloidal suspension is prepared as follows. A required amount of soluble potato starch is mixed with water and the solution is heated to boil, whereupon an aqueous solution of calcium hydroxide is added thereto. Water is then added to produce a suspension with the following ratio between the ingredients:

| | |
|---|---|
| calcium hydroxide, | 30 to 160 g/l |
| soluble potato starch, | 5 to 20 g/l. |

The blank 1 to be checked is placed on the roller bed 2. The surface of the blank 1 may be etched or milled, or worked with an abrasive disc or flame cutter. The blank 1 may also be checked right after hot rolling, with its surface coated with scale.

The roller bed 2 is brought into operation, and the blank 1 starts moving in the direction indicated by the arrow at a speed of 0.3 to 1 meter per second. As the front face of the blank 1 reaches the pulverizer, 3, the latter and the nozzle 5 are simultaneously actuated to apply the background component onto the surface of the blank 1 and dry it with a jet of hot air.

As the front face of the blank 1 reaches the pulverizer 4, the latter and the nozzle 6 are actuated to apply the contrast component onto the surface of the blank 1 and dry it with a jet of hot air. The temperature of the air coming from the nozzles 5 and 6 must be below the point at which thermochemical transformation of the contrast component takes place.

The consumption of the background and contrast components and of the colloidal suspension is 0.2 to 0.5 liter per square meter of a rolled product's surface.

Once the indicator coating is formed on the surface of the blank 1, the latter finds itself under the inductor 7 of the high-frequency generator 8. The inductor 7 induces eddy currents in the surface layer of the blank 1. The density of the eddy currents differs over the surface of the blank 1. In defective areas the density of the eddy currents is greater than over the rest of the blank's surface, so a local overheating is observed in said defective areas. The temperature gradient between the defective areas and the rest of the blank's surface is great enough to cause a thermochemical transformation and change of color of the contrast component of the indicator coating, whereas that coating remains intact over the rest of the blank's surface. Spots 9 of a color different from that of the indicator coating show the locations of surface and subsurface defects in the blank 1.

The function of the contrast component of the indicator coating may be performed by the following substances:

colloidal aqueous solutions of organic compounds, such as starch, soap, agar-agar, etc., in concentrations from 0.5 percent by weight to that of a saturated solution;

colloidal solutions of organosilicon compounds (resins);

aqueous solutions of high-molecular organic compounds, such as carbohydrates, in concentrations from 1.0 percent by weight to that of a saturated solution;

aqueous solutions of organic compounds which burn when heated to a temperature of 100° to 600° C., instead of decomposing, such as oxalic acid.

In the general case the high-frequency current heating of rolled products is effected as follows.

The shape and size of the inductor are selected in keeping with the general requirements and with due regard for the size of the rolled product and the curvature of its surface. The mean temperature to which the product's surface is heated must be 30° to 50° C. below the point at which thermochemical transformation of the contrast component of the indicator coating takes place.

The current frequency of the high-frequency generator depends upon the material of the rolled product being checked; the frequency is lower for ferromagnetic materials than for nonmagnetic materials. The speed of the rolled product's movement is determined by the desired checking rate or by the speed of the production line in which the fault detection device is incorporated.

The output of the high-frequency generator is selected in keeping with the general requirements and with due regard for the size of the rolled product to be checked, the size and shape of the inductor, as well as the mean temperature to which the surface of the product is to be heated and the speed at which the product moves along the roller bed.

The above data (size of the rolled product to be checked and the speed of its movement, the current frequency, and the output of the high-frequency generator) help to appropriately adjust the parameters of the inductor (the inductor's size, the dimensions of the conductor, and the number of turns) and thus make the high-frequency generator as economical as possible.

What is claimed is:

1. A method for detecting surface and subsurface flaws in rolled products, comprising applying an indicator coating, comprising a background component and a contrast component, onto the surface of a relatively cold rolled product, the contrast component being a heat-sensitive compound, and heating the rolled product with high-frequency currents to a temperature sufficiently high to produce a temperature gradient in defective areas and thus cause a thermochemical transformation of the contrast compound, accompanied by a change in its color, said indicator coating being a colloidal suspension comprising an aqueous solution of calcium hydroxide and soluble potato starch with the following ratio between the ingredients:

| calcium hydroxide, | 30 to 160 g/l |
| soluble potato starch, | 5 to 20 g/l. |

2. A method for detecting surface and subsurface flaws in rolled products, comprising applying an indicator coating, comprising a background component and a contrast component, onto the surface of a relatively cold rolled product, the contrast component being a heat-sensitive compound, and heating the rolled product with high-frequency currents to a temperature sufficiently high to produce a temperature gradient in defective areas and thus cause a thermochemical transformation of the contrast compound, accompanied by a change in its color, said background component being a compound which is light in color and does not undergo change over a temperature range of 200° to 300° C. and said contrast component undergoes thermochemical transformation with change in color at 200° to 300° C.

3. A method for detecting surface and subsurface flaws in rolled products, comprising applying an indicator coating, comprising a background component and a contrast component, onto the surface of a relatively cold rolled product, the contrast component being a heat-sensitive compound, and heating the rolled product with high-frequency currents to a temperature sufficiently high to produce a temperature gradient in defective areas and thus cause a thermochemical transformation of the contrast compound, accompanied by a change in its color, said indicator coating being applied to said product as a liquid as said product is being advanced in a direction of travel, said method further comprising drying said liquid product after its application onto said product prior to said heating.

4. A method as claimed in claim 2 or 3, wherein the indicator coating is formed by successively applying the background component and the contrast component onto the surface of the rolled product.

5. A method as claimed in claim 1, 2 or 3, wherein prior to being heated with high-frequency currents, the indicator coating is dried at a temperature below the point at which the thermochemical transformation of the contrast compound takes place.

6. A method as claimed in claim 2 or 3, whereby the indicator coating is produced by applying a colloidal suspension onto the rolled product.

7. A method as claimed in claim 1, 2 or 3 wherein said rolled products are hot rolled blanks and billets which have not been descaled.

8. A method as claimed in claim 2 or 3 wherein said background component is an aqueous solution of calcium hydroxide and said contrast component is an aqueous solution of potato starch.

* * * * *